(12) United States Patent
Hybertson et al.

(10) Patent No.: US 10,610,590 B2
(45) Date of Patent: Apr. 7, 2020

(54) ELECTROCHEMICAL PLASMA ACTIVATED AQUEOUS CHEMOTHERAPEUTICS

(71) Applicant: Symbios Technologies, Inc., Fort Collins, CO (US)

(72) Inventors: Brooks M. Hybertson, Boulder, CO (US); Jessica M. Joslin, Fort Collins, CO (US); Justin P. Bzdek, Fort Collins, CO (US); Derek C. Johnson, Fort Collins, CO (US)

(73) Assignee: Symbios Technologies, Inc., Fort Collins, CO (US)

( * ) Notice: Subject to any disclaimer, the term of this patent is extended or adjusted under 35 U.S.C. 154(b) by 0 days.

(21) Appl. No.: 15/585,084

(22) Filed: May 2, 2017

(65) Prior Publication Data

US 2017/0312362 A1 Nov. 2, 2017

Related U.S. Application Data

(60) Provisional application No. 62/330,713, filed on May 2, 2016.

(51) Int. Cl.

| | | |
|---|---|---|
| *A61K 41/00* | (2020.01) | |
| *A61K 9/08* | (2006.01) | |
| *A61K 45/06* | (2006.01) | |
| *A61K 47/02* | (2006.01) | |
| *A61K 33/14* | (2006.01) | |
| *A61K 9/00* | (2006.01) | |
| *A61K 33/00* | (2006.01) | |

(52) U.S. Cl.
CPC ........ *A61K 41/0023* (2013.01); *A61K 9/0019* (2013.01); *A61K 9/08* (2013.01); *A61K 33/00* (2013.01); *A61K 33/14* (2013.01); *A61K 45/06* (2013.01); *A61K 47/02* (2013.01)

(58) Field of Classification Search
CPC .............. A61K 2039/852; A61K 41/00; A61K 41/0009; A61K 41/0023
See application file for complete search history.

(56) References Cited

U.S. PATENT DOCUMENTS

2004/0007539 A1 * 1/2004 Denes ................... C02F 1/4608
210/748.18

OTHER PUBLICATIONS

Hattori et al (Effectiveness of plasma treatment on pancreatic cancer cells, International Journal of Oncology 17: 1655-1662, 2015) (Year: 2015).*

Taylor et al (Long-term antibacterial efficacy of air plasma-activated water, Journal of Physics D: Applied Physics, 44, 2011). (Year: 2011).*

* cited by examiner

*Primary Examiner* — Micah Paul Young

(74) *Attorney, Agent, or Firm* — Samuel M. Freund; Cochran Freund & Young LLC

(57) ABSTRACT

Methods for the generation of electrochemical plasma activated aqueous chemotherapeutics (EPAAC) solutions are described. These solutions have been found to selectively reduce the proliferation of human pancreatic cancer cells, with no toxic effects for healthy cells.

22 Claims, 7 Drawing Sheets

ELECTROCHEMICAL PLASMA ACTIVATED AQUEOUS CHEMOTHERAPEUTICS

CROSS-REFERENCE TO RELATED APPLICATIONS

The present application claims the benefit of U.S. Provisional Patent Application No. 62/330,713 for "Methods and Applications of Electrochemical Plasma Activated Aqueous Chemotherapeutics" by Brooks M. Hybertson et al., which was filed on 2 May 2016, the entire contents of which patent application is hereby specifically incorporated by reference herein for all that it discloses and teaches.

BACKGROUND

In recent years, the physicochemical characteristics of non-thermal plasmas have been extensively studied in the field of Plasma Medicine, including preliminary investigations of possible use to treat biological disorders such as infections, wounds, and cancer. Plasma refers to an ionized, electronically-excited gas that contains ions, radicals, and electrons. The term non-thermal indicates a plasma comprised of gas atoms, molecules, and ions in which their kinetic energy is low enough that the overall fluid temperature remains close to, or at, room temperature while the electrons encompassed in the plasma contain higher amounts of energy. This additional kinetic energy allows the electrons to induce the cleavage of chemical bonds, but the low overall kinetic energy of the plasma can suppress the complete atomization of the molecule.

Non-thermal plasma species identified for interaction with biological systems including cancer cells include hydrogen peroxide, ozone, nitrite anion, and nitrate anion, with additional species such as peroxynitrite anion, other NOR, free radical, and short- or long-lived reactive intermediates being generated. Notably, the combination of plasma species appears to be more potent than individual chemical components. The selectivity of non-thermal plasma species at inhibiting cancer cells, but not normal cells, in prior work, demonstrates promise for the field of Plasma Medicine relating to cancer treatments.

SUMMARY

To achieve the purposes of embodiments of the present invention, as embodied and broadly described herein, the method for treating pancreatic cancer hereof, includes: providing a solution having a chosen quantity of sodium chloride dissolved in water; providing an apparatus comprising: a chamber for containing the solution, the chamber having an electrically conducting cylindrical wall having an axis, an inlet for the solution at one end thereof and an outlet for the solution at the opposing end thereof; an elongated hollow, electrically conducting shaft rotatably disposed collinearly with the axis of the cylindrical portion of the chamber and having an open end and a closed end, the closed end thereof facing the end of the chamber having the inlet for the solution; at least one electrically conducting pin electrode having a bore therethrough, a first end and a second end, and having a frit effective for generating bubbles in the solution at the surface of the at least one pin electrode from which a plasma discharge is generated, disposed in the bore in the vicinity of the first end thereof, the second end being mounted through the surface of the shaft such that the bore of the at least one pin electrode is in gaseous communication with the interior of the hollow shaft; an electrically insulating cylinder having an axis collinear with the axis of the chamber disposed within the chamber, the electrically insulating cylinder having a surface through which a portion of the at least one pin electrode extends, the electrically insulating cylinder rotating with the shaft; a motor for rotating the shaft; a solution inlet for introducing the solution into the inlet of the chamber such that the solution flows axially in the cylindrical portion of the chamber; a gas source for introducing a chosen gas into the open end of the shaft at a pressure such that gas bubbles exit through the frit of the at least one pin electrode and rise in a counter-current manner to the flow of the solution; and an electrical power supply for applying a voltage to the shaft effective for initiating and maintaining the plasma discharge between the first end of the at least one pin electrode and the interior of the conducting cylindrical portion of the chamber; introducing the solution into the chamber through the solution inlet; introducing the chosen gas from the gas source into the open end of the shaft; rotating the shaft at a chosen rotational rate using the motor; applying a selected voltage from the power supply to the shaft, whereby a plasma discharge is generated; exposing the solution to the plasma for a selected period of time, forming thereby a plasma activated solution having a pH; and exposing cells afflicted with pancreatic cancer to the plasma activated solution.

In another aspect of embodiments of the present invention and in accordance with its purposes the method for treating pancreatic cancer hereof, includes: providing a solution having a chosen quantity of a single sodium chloride solute dissolved in water; generating a plasma in the single sodium chloride solute solution for a selected period of time, forming thereby a plasma activated solution having a pH; adding a base to the plasma activated solution to adjust the pH to 7.4±0.1, forming thereby a physiological solution; adding sodium chloride to the physiological solution to adjust the chosen quantity of sodium chloride to 9±0.1 g per liter of solution, forming thereby an isotonic solution; and exposing cells afflicted with pancreatic cancer to the isotonic solution.

Benefits and advantages of embodiments of the present invention include, but are not limited to, providing a method for generating electrochemical plasma activated solutions which are selective in reducing the proliferation of pancreatic cancer cells, while exhibiting minimal cytotoxic effects on healthy cells, such as smooth muscle cells, endothelial cells, and other organ-specific cells.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1A:
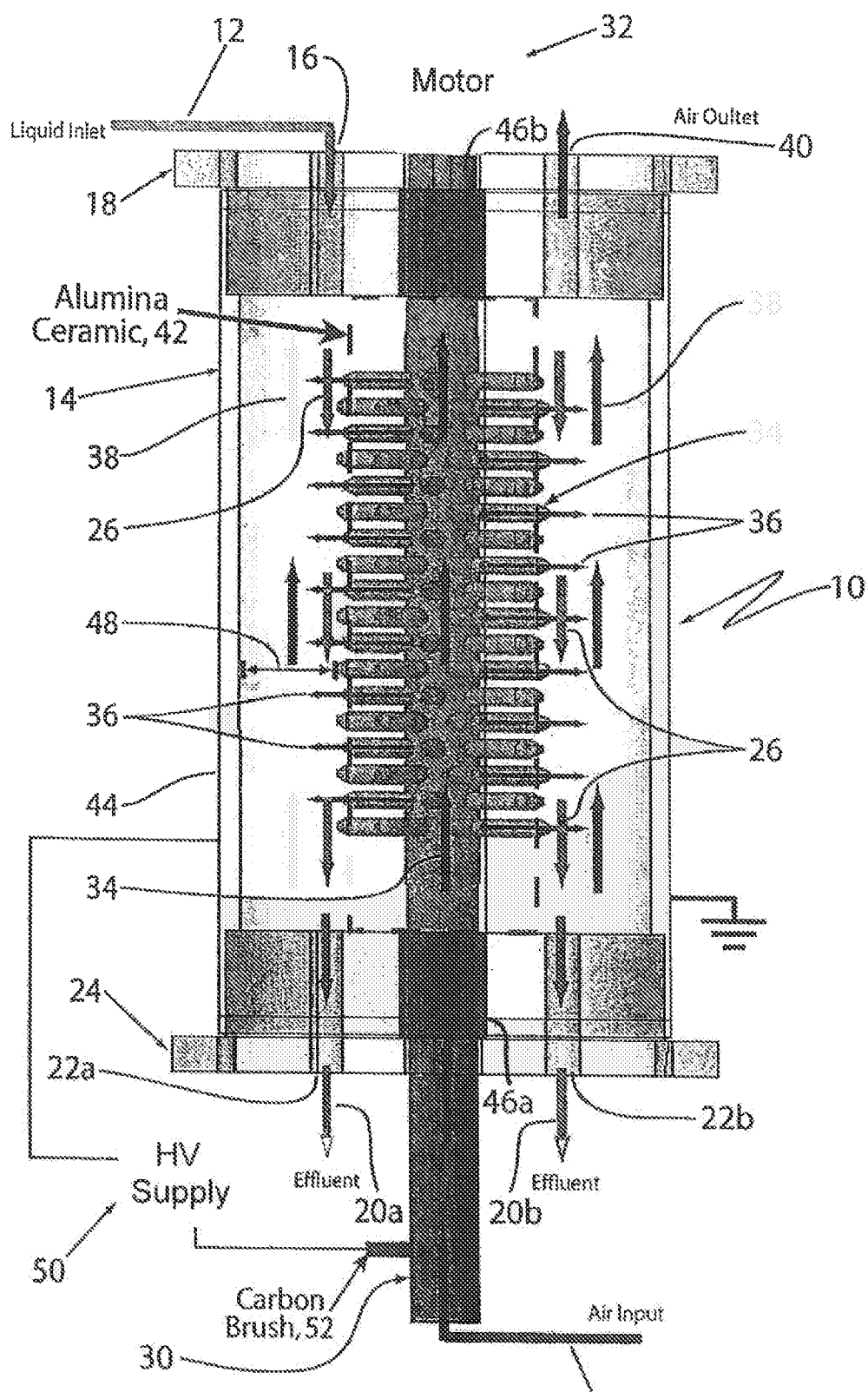
FIG. 1A is a schematic representation of a perspective view of an embodiment of the tubular high-density plasma reactor (THDPR) used to generate the activated aqueous chemotherapeutic solutions hereof, illustrating the fluid and gas flow and a pin electrode configuration.

In accordance with embodiments of the present invention, activated species generated in aqueous solutions of sodium chloride in a tubular, high-density plasma reactor, described in detail below, and termed as electrochemical plasma activated aqueous chemotherapeutics (EPAAC), or aqueous plasma chemotherapeutics (APC), have been used for treatment of pancreatic cancer. The EPAAC solution may be directly administered to the pancreas for a localized effect by use of a catheter or syringe or by intravenous administration. The EPAAC solution is useful as a cancer therapy due to its ability to selectively inhibit the proliferation of human pancreatic cancer cells, while exhibiting non-toxic behavior toward normal human cells. Such solutions have been found to selectively and efficiently inhibit cancer cell proliferation on the same order, or even more efficiently, than established chemotherapeutic drugs while mitigating cytotoxic effects. Notably, common small-molecule chemotherapy drugs are not selective in nature, thus, normal cells are targeted alongside cancer cells, resulting in undesirable and damaging side effects. The selectivity and mechanism of action for EPAAC solutions is expected to be dependent upon solution composition and electrochemical treatment parameters. Treatment of pancreatic cancer may employ EPAAC alone, or in combination with chemotherapeutic or other additives to result in enhanced cellular uptake of drugs for improved oncological performance.

Reference will now be made in detail to the present embodiments of the invention, examples of which are illustrated in the accompanying drawings. In the FIGURES, similar structure will be identified using identical reference characters. It will be understood that the FIGURES are presented for the purpose of describing particular embodiments of the invention and are not intended to limit the invention thereto.

A. Apparatus:

Turning first to FIG. 1, a schematic representation of a perspective view of an embodiment of the tubular high-density plasma reactor, 10, used to prepare EPAAC solutions in accordance with embodiments of the present invention is shown, illustrating sodium chloride solution, 12, entering tubular chamber or container, 14, through inlet, 16, in upper flange, 18, exiting as a plasma activated solution, 20a, and, 20b, through outlets, 22a, and, 22b, respectively, in lower flange, 24, thereof, after traveling axially, 26, through tube 14. House air, 28, is introduced into solution 26 through hollow, rotatable, electrically conducting shaft, 30. A flow rate of about 200 SCFH was employed in the EXAMPLES. Shaft 30 is rotatably driven by motor, 32, and supports a chosen configuration of hollow pin discharge electrodes, 34, affixed thereto and in communication with air 36 from air source 28. Air exiting, 36, from hollow pins 34 rises, 38, flowing counter-currently to solution 26, and exits container 14 through orifice, 40, in upper flange 18, which may include a valve. The solution travels the axial length of reactor 10 and plasma activated solution exits through liquid orifices 22a and 22b which may include release valves at the bottom of the reactor. As will be discussed below, the air introduction system is designed such that only a radial pressure gradient exists between the inner shaft and outer cylinder, thereby ensuring an equal volumetric flow rate of the air through the bores of pin electrodes 34, independent of their position along shaft 30.

As illustrated in FIG. 1A, hollow pin electrodes 34 protrude outward from shaft 30, through insulating cylinder, 42, that may be fabricated from ceramic or Teflon, as examples, which rotates with shaft 30, toward the outer stationary cylinder, 44, of container 14, and may be arranged such that approximately 100 discharge electrodes are disposed on a one foot length of shaft 30. Hollow pin electrodes 34 may be fabricated using stainless steel, tungsten, titanium, or molybdenum, as examples, although stainless steel electrodes were employed in the generation of the EPAAC solutions in the EXAMPLES. Motor 32 is effective for rotating shaft 30 at a rate of between about 60 rpm and about 5000 rpm, on bearings, 46a, and, 46b. About 1000 rpm was employed in preparing the EPAAC solutions. Gaps, 48, between the tips of discharge electrodes 34 and outer cylinder 44 can be adjusted to distances between about 0.5 mm and approximately 3 mm. An approximately 2 mm gap was used in the EXAMPLES.

A plasma discharge is initiated at the outer tip of discharge electrodes 34 and propagates to the inner wall of stationary outer cylinder 44. An electrical power supply, 50, capable of supplying between 0.5 kV and 1 kV is effective for initiating and maintaining this discharge, and is placed in electrical connection with conducting shaft 30 using carbon brush, 52, as an example, for which the return connection to complete the circuit is in contact with stationary outer cylinder 44. Typical voltages used to prepare the EPAAC were between about 250 V and about 750 V. Between approximately 0.5 A and about 3 A of current were applied. During exposure, fluid temperature was found to increase between about 0° C. and about 30° C. To date only DC voltages have been used; however, AC or pulsed operating modes may also be employed. Bearings 46a and 46b are insulated to ensure that neither the inner shaft nor the outer stationary cylinder becomes charged. Tubular plasma reactor 10 is expected to maximize the time in which a solution element moving axially through the reactor is in contact with the plasma. This is accomplished by minimizing the distance that the pin electrodes protrude from insulating cylinder 42 of the rotating shaft 30.

Figure 1B:
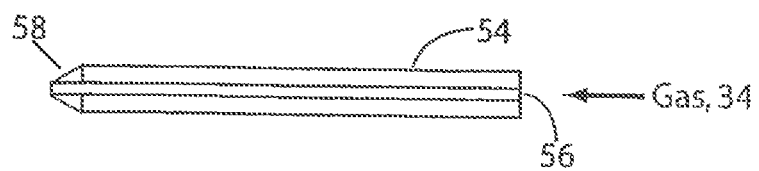
FIG. 1B is a schematic representation of the side view of an unmodified pin electrode.
Figure 1C:
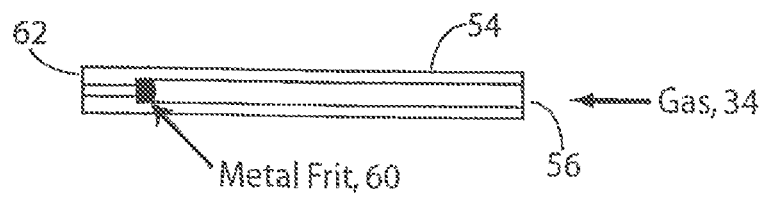
FIG. 1C is a schematic representation of the side view of a pin electrode in which a frit is inserted into the bore thereof.

FIG. 1B is a schematic representation of the side view of unmodified pin electrode, 54, having bore, 56, and tapered tip, 58, disposed at the discharge end of pin electrode 54. FIG. 1C is a schematic representation of the side view of pin electrode 54 in which frit, 60, is inserted into bore 56 in the vicinity of the discharge end, 62, thereof. Frit 60 may be a commercially available metal or glass frit having appropriate structural integrity. Equal volumetric flow rates of the air through the bores of pin electrodes 34, independent of their position along shaft 30, may be obtained by restricting the air flow using appropriate frits. Additional details of apparatus 10 may be found in U.S. Pat. No. 9,346,691, the entire contents of which is hereby incorporated by reference herein for all that it discloses and teaches.

Solution was circulated at about 2.6 gph (gallon per hour) through a reactor volume of approximately 225 mL to achieve a given residence time; additional combinations of flow rates and liquid volumes may be employed to achieve a selected fluid plasma-exposure residence time.

B. Influent:

The influent solution can be prepared with variable quality of water, ranging from sterilized water for injection (WFI) to nanopure, deionized, or tap water, since the inherent sterilization processes that occur during plasma treatment impart a sterile nature to the water that is treated. Total dissolved solids (TDS) concentration of the initial influent water may range from 0 to greater than 15,000 mg/L, or more advantageously between 1,000-7,000 mg/L. As stated above, the initial solution contained sodium chloride in the absence of other solutes. Initial chloride ion levels can impact the intermediate chemical species, both short- and long-lived, that form during the treatment period, since the presence of chloride is known to accelerate ozone decomposition in aqueous solution. Other additives may include, but are not limited, to salts, sugars, vitamins, alcohols, ketones, acids, buffers, and drugs. Solution pH may have an effect in controlling the resulting reactive species that form. The EXAMPLES describe an initial influent composition comprised of 1000 mg/L USP-grade sodium chloride (NaCl), in the absence of other solutes, prepared in sterile water for injection.

If chlorinated intermediates are not desired, alternate salts can be employed to contribute to solution conductivity, but not result in chlorinated species. Other intermediate pathways may be favored with the addition of nitrite or nitrate salts, as examples. Additionally, the concentration of ions in solution may alter the fraction of applied current that contributes to conductive pathways through the solution as opposed to plasma pathways. As an example, lower saline content will lower solution conductivity, thus making plasma discharge the dominant current pathway.

C. Effluent Post-Processing:

The effluent solution may be modified post-processing to adjust the final properties of the EPAAC solution prior to administration as a therapeutic agent. As an example, for subsequent biological application, the TDS of the final product can be adjusted to approximately the isotonic range (9 g/L saline) by addition of sodium chloride. Additionally, the pH of the solution can be adjusted to be about the physiological pH value 7.4. Other processing steps may include centrifugation or filtration.

Therapeutic agents, such as chemotherapeutics and other drugs, can be added to the EPAAC solution for increased efficacy of the desired therapeutic outcome. The recovered EPAAC solution can be modified by addition of salts, sugars, vitamins, buffers, proteins, enzymes and drugs or drug pre-cursors.

D. EPAAC Solutions for Cancer Therapy:

EPAAC solutions have demonstrated cancer cell growth inhibition selectivity. The EPAAC solution can be administered as a direct (stand-alone) therapeutic, or in combination with other components. In accordance with their stability, the solutions may be stored in bags and distributed for later clinical use. The shelf lives of the EPAAC solutions investigated have been found to be on the order of days or weeks.

Reactor systems may be delivered to treatment sites for on-site generation of EPAAC solution for patient administration. As an example, EPAAC solutions may be drawn into a syringe and injected subcutaneously in the vicinity of or directly into the pancreas of a patient for localized treatment, or intravenously injected into a patient for systemic treatment. Other routes of administration include the use of catheters and cannulas, as examples.

The EPAAC solutions generated in accordance with the teachings of embodiments of the present invention has been found to be selective in reducing the proliferation of pancreatic cancer cells, while exhibiting minimal cytotoxic effects on healthy cells, such as smooth muscle cells, endothelial cells, and other organ-specific cells.

Having generally described embodiments of the present invention, the following EXAMPLES provide additional details.

a. Apparatus Parameters:

In what follows, an approximately 2 mm electrode gap, an about 200 SCFH flow of house air, an approximately 1000 rpm rotation rate (shaft 30), an about 2.6 gph flow rate through an approximately 225 mL reactor volume, and an about 3 A steady-state DC current were used. The solutions were treated for about 5 min. in a recirculation mode. The solution can be recirculated through a single reactor to increase the concentration of the activated aqueous species present in solution by increasing the solution residence time in the reactor, or the effluent from one reactor can be introduced into a second reactor in series with the first. The inlet gas used during the plasma generation can also significantly impact the intermediates generated, such as the increased formation of $NO_x$ species (i.e. nitrite/nitrate and their corresponding acids) with the use of air and $N_2$ as the inlet gas when compared to using high-purity $O_2$. Further, the use of inert gases, such as argon, for atmospheric plasma discharges has been found to yield hydrogen peroxide-dominated solution chemistries, whereas inclusion of oxygen yields mechanisms that favor atomic oxygen with subsequent chlorine chemistries.

b. Cell Lines and Culture:

All cells were purchased from publicly available sources, were not modified, and were handled according to supplier specifications for complete growth medium, culturing, subculturing, and cryopreservation protocols. All media formulations were obtained from publicly available sources and prepared according to supplier specification and standard cell culture practices under sterile conditions. All live cells were received from the supplier under cryopreservation and cultured according to standard practices.

All lines used were adherent human cell lines.
  (i) Pancreatic cancer cell line: MIA PaCa-2
    Source: Available from ATCC (ATCC® CRL1420™)
    Complete growth medium: Eagle's Minimum Essential Medium containing 5% fetal bovine serum and 5% cosmic calf serum
  (ii) Human umbilical vein endothelial cells: HUVEC
    Source: Available from ATCC (ATCC® PCS-100-010™) or Lonza (single or pooled donor)
    Complete growth medium: EGM-2 BulletKit (Lonza)
  (iii) Human foreskin fibroblasts: HFF-1
    Source: Available from ATCC (ATCC® SCRC-1041™)
    Complete growth medium: Dulbecco's Modified Eagle's Medium containing 15% fetal bovine serum
  (iv) Immortalized pancreas duct epithelial-like cells: hTERT-HPNE
    Source: Available from ATCC (ATCC® CRL4023™)
    Complete growth medium: Specialty Dulbecco's Modified Eagle's Medium composition, protocol available from ATCC
  (v) Primary pancreatic stellate cells: Panc stellate
    Source: Available from Applied Biological Materials (T4215)
    Complete growth medium: Prigrow I containing 10% fetal bovine serum.

Each cell line was adherent in a growth flask, incubated at 37° C. and 5% $CO_2$; de-attached cell from growth flask using Trypsin-EDTA solution (0.25% Trypsin, 0.53 mM EDTA); and counted by Trypan blue staining standard protocol. Split cells were handled according to supplier specification during culture.

Cell Proliferation Assay:

A standard cell proliferation assay was used, the Alamar blue assay, to assess quantification of viable cells. This assay is a well-established method in the scientific community and test kits and protocols are publicly available; for example, a test kit is available from Thermo Fisher Scientific. A probe compound, resazurin, was added to complete growth medium to which the adhered cells were exposed in a standard 96-well plate format. In the presence of metabolic cellular activity, resazurin is converted to resorufin, a fluorescent product. The fluorescence measured in the solution is thus proportional to the amount of live cells present at the end of an assay period. This is a standard method for measuring cell proliferation.

i. Day 1: Cell Seeding:
    All cell lines were collected, counted, and diluted according to the same procedure to obtain a 10,000 cell/mL suspension of cells in complete growth medium;
    Each cell line was plated (seeded) in a 96-well plate layout using commercially available Thermo Scientific™ Nunc™ MicroWell™ 96-Well Microplates containing a Nunclon™ Delta cell culture treated surface to promote cell attachment and growth. Such plates are standard for antibiotic screens, cell-based assays, and screening compounds; and Plates were incubated for 24 h to allow cell attachment and proliferation on the plate surface
  ii. Day 2: Dosing:
    For all plates, complete growth medium was removed from all wells and replaced with fresh growth medium at volumes specific to the dose dilution for that well (see TABLE below);
    For APC dosing, APC was aliquoted into complete growth medium in each well at a volume specific to the desired v/v % APC concentration:

TABLE

| % APC | $V_{APC}$ (μL) | $V_{media}$ (μL) |
|---|---|---|
| 50 | 100 | 100 |
| 25 | 50 | 150 |
| 12.5 | 25 | 175 |
| 5 | 10 | 190 |
| 1 | 2 | 198 |
| 0 (Control) | 0 | 200 |

For positive control, cells were independently dosed with a carboplatin chemotherapeutic drug to ensure correct cellular growth behavior. The dosing procedure was accomplished similarly to that of APC; and
  Plates were incubated for 72 h to allow impact of drug (APC or carboplatin) on cells, followed by growth of cells to assess ultimate impact of the drug on cell growth, according to standard practice.
  iii. Day 5: Reading
    For all plates, the complete growth medium/drug solutions were removed and the remaining adhered cells rinsed with phosphate buffered saline to remove any residual drug that could interfere with the fluorescent assay; cells remained adhered to the well during this step;
    To each well, fresh complete growth medium was added;
    To each well, Alamar blue solution was added at 10 v/v % of the amount of complete growth medium;
    Plates were incubated for 1 h to allow the conversion reaction to the fluorescent product as a result of cellular metabolic activity to take place;
    Plates were read using a fluorescent microtiter plate reader according to standard procedure; the excitation wavelength ($\lambda_{ex}$) at 530 nm and the emission wavelength ($\lambda_{em}$) at 590 nm; and
    All fluorescent counts were normalized by the control response (no drug, wells containing only cells and 100% complete growth medium over the duration of the cell culture assay).

Example 1

EXAMPLE 1 illustrates one method of producing APC solution and its subsequent action on pancreatic cancer cells compared to a commercially available small molecule chemotherapeutic and a saline solution control. APC solution was prepared by adding 1000 mg/L USP-grade sodium chloride (NaCl) salt to 1 L of water for injection (WFI) in a sterile 1 L glass container. The influent solution was treated in the tubular high-density plasma reactor, THDPR under the following conditions: 2 mm electrode gap, introduction of 200 SCFH of house air, rotor spin rate of 1000 rpm. Once the reactor fill volume of 225 mL was achieved, continuous flow was achieved via peristaltic pumping at 2.6 gph flow rate in a recirculation loop. Plasma discharge was initiated by applying a 3 A steady-state current to the system. The solution was recirculated such that the same 1 L volume cycled continuously from the reservoir to the reactor for treatment. After a 5 min. treatment time, corresponding to an about 1 min. residence time of plasma exposure, the current was stopped and the plasma-treated solution was recovered.

The recovered solution was centrifuged, the supernatant solution was pH adjusted to about 7.4 by addition of strong base (0.1 M NaOH), and brought to isotonic by addition of USP-grade NaCl to reach 9000 mg/L total dissolved solids. Within approximately 1 h of solution preparation, seeded MIA PaCa-2 cells adhered to the bottom of 96-well plates were dosed with APC solution at the following concentrations relative to the total volume (200 µL) in the well: 1, 5, 12.5, 25, and 50 v/v %, the remaining volume being composed of cell medium. Control cells were also dosed with the isotonic saline solution treated in the same manner as the APC, without the plasma treatment. A positive control was included by dosing the MIA PaCa-2 cells with carboplatin at concentrations of 0.2, 1, 2.5, 5, and 10 µg/mL, which is an established therapeutic range for carboplatin.

Cell proliferation was assessed after a 72 h incubation period, whereby the cells were rinsed with phosphate buffered saline, PBS, given fresh media, and subsequently reacted with Alamar blue, which was converted to the fluorescent product, resorufin, in the presence of metabolically active cells. The fluorescence counts were read using a microtiter plate reader to determine the fraction of live cells compared to the control cell wells exposed only to media.

Figure 2:
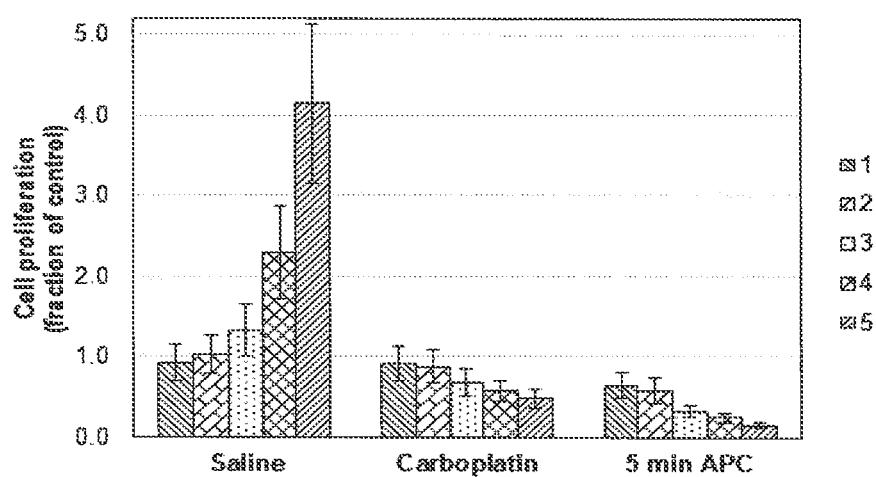
FIG. 2 shows graphs of human pancreatic cell proliferation for saline control solution, carboplatin positive control drug, and 5 min. electrochemical plasma activated aqueous chemotherapeutics (EPAAC) solution, referred to here as aqueous plasma chemotherapeutics (APC), where the following dosages were administered to the cancer cells diluted in appropriate complete growth medium for each cell type: (1) 1 v/v % for saline and 5 min. APC, 0.2 µg/mL for carboplatin; (2) 5 v/v % for saline and 5 min APC, 1 µg/mL for carboplatin; (3) 12.5 v/v % for saline and 5 min. APC, 2.5 µg/mL for carboplatin; (4) 25 v/v % for saline and 5 min. APC, 5 µg/mL for carboplatin; and (5) 50 v/v % for saline and 5 min. APC, 10 µg/mL for carboplatin.

FIG. 2 shows graphs of human pancreatic cell proliferation for saline, carboplatin, and 5 min. APC, where the following dosages were administered to the cancer cells: (1) 1 v/v % for saline and 5 min. APC, 0.2 µg/mL for carboplatin; (2) 5 v/v % for saline and 5 min. APC, 1 µg/mL for carboplatin; (3) 12.5 v/v % for saline and 5 min. APC, 2.5 µg/mL for carboplatin; (4) 25 v/v % for saline and 5 min. APC, 5 µg/mL for carboplatin; and (5) 50 v/v % for saline and 5 min. APC, 10 µg/mL for carboplatin. It may be observed that the saline solution yielded a dose-dependent proliferation of cancer cells. However, the carboplatin and APC solutions yielded dose dependent cell growth inhibition, where at a dosage range indicated, the APC was at least as effective as the carboplatin. These results demonstrate the dose-dependent response of inhibition of pancreatic cancer cell growth using an APC solution. Thus, this method represents a treatment of pancreatic cancer. Efficacy of EPAAC solutions against pancreatic cancer cells has thus been demonstrated in the dosage range of 1-50 v/v %.

Example 2

Figure 3:
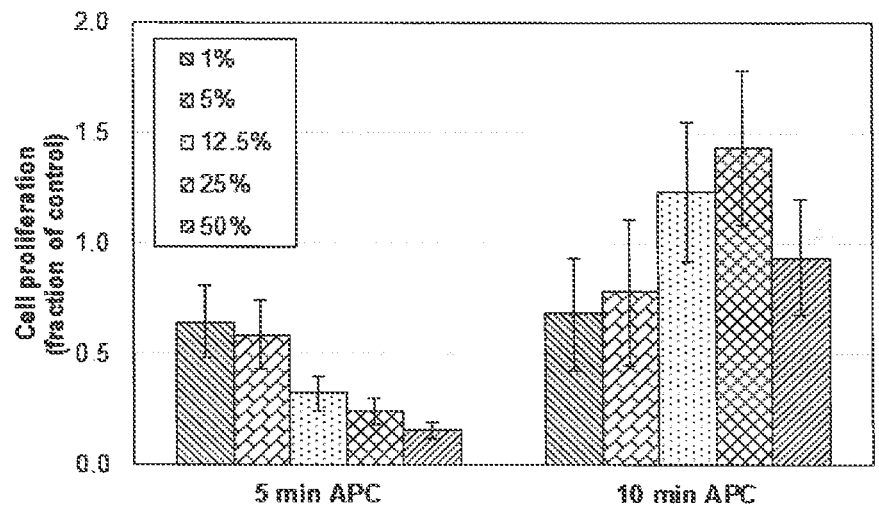
FIG. 3 shows graphs of human pancreatic cancer cell proliferation as a function of dosage for 5 min. and 10 min. APC, for the following dosages: 1, 5, 12.5, 25, and 50 v/v %, illustrating that dose-dependent cell proliferation inhibition occurs for the 5 min. APC solution, whereas the 10 min. APC does not yield a dose-dependent cell proliferation inhibition.

EXAMPLE 2 illustrates the effect of plasma residence time on the subsequent chemotherapeutic activity of the APC solution. APC solution was prepared according to the description in EXAMPLE 1; however, in addition to a 5 min. treatment time (~1 min residence time), a 10 min. treatment time was also employed (~2.5 min. residence time). MIA PaCa-2 pancreatic cancer cells were dosed with the 5 and 10 min. APC solutions, and a proliferation assay performed. FIG. 3 are graphs of human pancreatic cancer cell proliferation as a function of dosage for 5 min. and 10 min. APC solutions, for the following dosages: 1, 5, 12.5, 25, and 50 v/v %. It may be observed from FIG. 3 that dose-dependent cell proliferation inhibition occurs for the 5 min. APC solution, whereas the 10 min. APC does not yield a dose-dependent cell proliferation inhibition, thereby indicating that the resulting chemotherapeutic activity may be related to the plasma treatment time associated with the APC solution preparation.

Example 3

Figure 4:
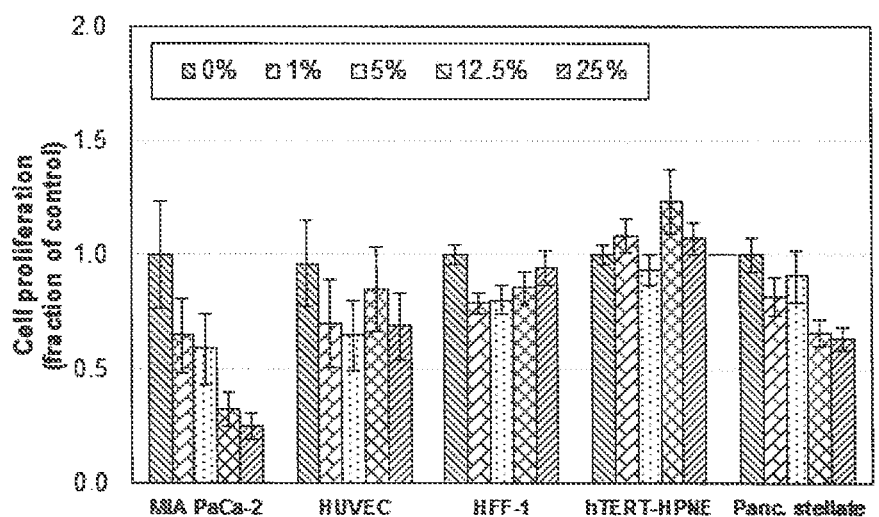
FIG. 4 shows graphs of cell proliferation for several human cell species as a function of APC solution dosage for the following dosages: 1, 5, 12.5, 25, and 50 v/v %, illustrating the non-toxic nature of APC solutions when administered to a variety of normal human cell lines.

FIG. 4 shows graphs of cell proliferation for several human cell lines as a function of APC solution dosage for the following dosages: 1, 5, 12.5, 25, and 50 v/v %, illustrating the non-toxic nature of APC solutions when administered to a variety of normal human cell lines. The APC solution generation was accomplished according to the description in EXAMPLE 1, where the APC solution was administered to adherent human normal healthy cells in addition to human cancer cells; more specifically, human umbilical vein endothelial cells (HUVEC), human foreskin fibroblasts (HFF-1), immortalized pancreas duct epithelial-like cells (hTERT-HPNE), and primary pancreatic stellate cells (Panc. stellate), were employed as control cell lines. It may be observed that the 5 min. APC solutions yielded a dose-dependent growth inhibition of the MIA PaCa-2 cancer cells, whereas the 5 min. APC solutions failed to exert similar growth inhibition when applied to a variety of healthy human control cell lines. More specifically, the HUVEC, HFF-1, and hTERT-HPNE control lines were unaffected by APC solution treatment with 77, 88, and 106% average viability, respectively, across all concentrations of APC solutions applied. The Panc. stellate control line did exhibit some growth inhibition at the higher 12.5 and 25 v/v % APC concentrations, but the viable cell number was still greater than the MIA PaCa-2 cells at those APC concentrations. These results indicate the ability of APC to selectively treat of cancer cells while remaining non-toxic to healthy cells.

Example 4

Figure 5:
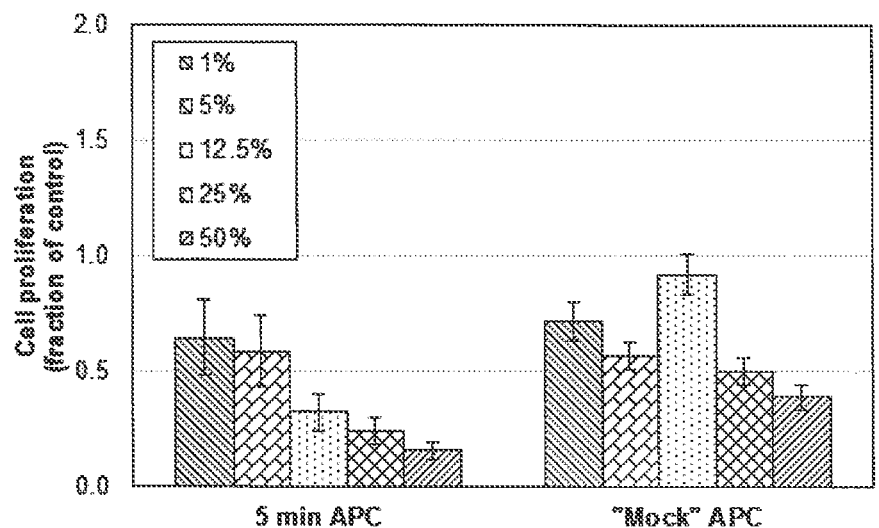
FIG. 5 shows graphs of human pancreatic cancer cell proliferation for APC solution and a "mock" APC solution, for the following dosages: 1, 5, 12.5, 25, and 50 v/v %, illustrating that the "mock" APC solution does not yield the same dose-dependent pancreatic cancer cell growth inhibition as does the APC solution.

EXAMPLE 4 illustrates that the stable oxidant species alone are not responsible for the therapeutic efficacy of the APC solution, and that the electrical discharge step is a required step. There are several stable oxidant species that survive downstream of the electrolytic process, which contribute to the overall oxidant levels. More specifically, the following levels of oxidants have been measured: 0.5-1 mg/L free chlorine, 1-10 mg/L hydrogen peroxide ($H_2O_2$), 0.25-1 mg/L ozone ($O_3$), 9 µM nitrite ($NO_2^-$) and 6.5 µM nitrate ($NO_3^-$). For consideration of whether the therapeutic effects of the APC solution can be accounted for by adding stable oxidant reagents to solution without the electrolytic processing step, a "mock" APC solution was generated. The "mock" APC solution contained the oxidant species that have been measured in APC solutions: 0.6 mg/L free chlorine, 1 mg/L hydrogen peroxide, 9 µM nitrite, and 6.5 µM nitrate. Additionally, the saline and pH levels were the same as the APC solution administered to cells. Note that due to the transient nature of ozone, ozone was not included in the "mock" APC solution. FIG. 5 shows graphs of human pancreatic cancer cell proliferation for APC solution and a "mock" APC solution, for the following dosages: 1, 5, 12.5, 25, and 50 v/v %, illustrating that the "mock" APC solution does not yield the same dose-dependent pancreatic cancer cell growth inhibition as does the APC solution. Thus, the therapeutic effects of APC solutions are dependent on the plasma-specific species generated.

Example 5

Figure 6:
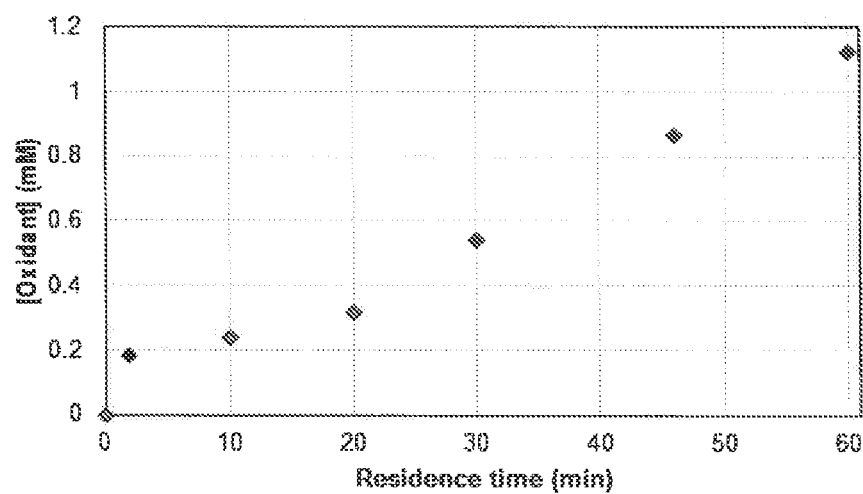
FIG. 6 is a graph of the oxidant level as a function of residence time in the plasma, illustrating that the oxidant level increases as a function of increasing residence time in the reactor.

EXAMPLE 5 illustrates how the plasma residence time will impact the oxidant species generated in the final APC solution, thus directly impacting its therapeutic efficacy. Employing an established oxidant analysis method, the total oxidant levels were measured as a function of residence time of ultra-pure water as exposed to plasma. The total oxidant levels were quantified using a derivatization assay employed whereby triphenylphosphine (TPP) is oxidized to TPPO in the presence of oxidant species, where the TPPO product is detected via HPLC-UV (Pinkernell et al., *Anal. Chem.* 69:3623-3627, 1997). FIG. 6 is a graph of the oxidant level as a function of residence time in the plasma, illustrating that the oxidant level increases as a function of increasing residence time in the reactor.

In many other experiments employing the plasma system described, the extent of oxidation of a surrogate molecule is directly related to the treatment time. More specifically, since the residence time of the solution in the plasma reactor is dependent upon both the solution flow rate and the average volume of solution in the reactor, decreasing the flow rate for a fixed volume will increase the residence time and vice-versa. Consistently, over a variety of different parameters, when the flow rate was doubled from 3 gph to 6 gph, there was a decrease in the ability of the effluent solution to chemically modify surrogate molecules. For example, utilizing the THDPR generating plasma under conditions in which the submersed pin electrodes are rotating at rates capable of inducing turbulent flow conditions within the reactor with an electrode distance of 1.5 mm, defined as the distance between the rotating pin electrodes and stationary outer electrode, an input current of 3 A, a reactor volume of 400 mL, and a flow rate of 3 gph (corresponding to a 2 min. residence time), a 15% reduction in the concentration of methylene blue was observed, indicating a chemical modification of the surrogate molecule. When the flow rate was increased to 6 gph (1 min. residence time), less than a 5% decrease in methylene blue concentration was observed due to an overall decrease in reactivity of the chemical intermediate species formed for the lower-residence-time trials where the water was in contact with the plasma/electrochemical process for a shorter period of time.

Example 6

Figure 7:
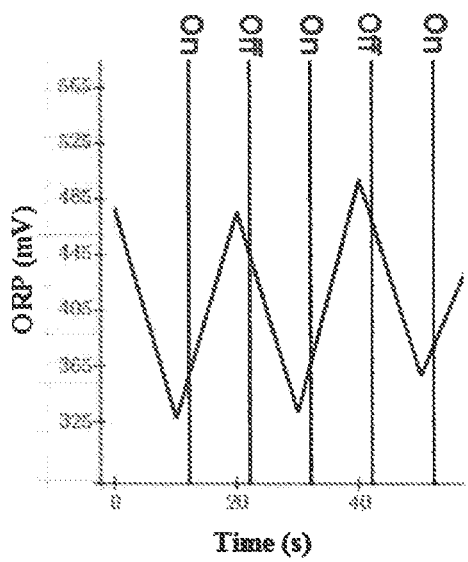
FIG. 7 is a graph of the measured ORP as a function of time for a specific example of a 300 mg/L TDS influent solution where the power was turned on and off to yield periods of plasma discharge and no current flowing, respectively, illustrating that the measured ORP of the solution increases when the plasma is on, and decreases when the plasma is off.

The oxidation-reduction potential (ORP) is a common measure of aqueous solution chemical species reactivity. In the above EXAMPLES, plasma discharges were employed during the duration of the solution treatment time. EXAMPLE 6 describes the dependence of solution ORP on plasma discharges during plasma on/off cycles, where no current was being applied during the off cycle. FIG. 7 is a graph of the measured ORP as a function of time for a specific example of a 300 mg/L TDS influent solution where the power was turned on and off to yield periods of plasma discharge and no current flowing, respectively. When plasma was discharged, the ORP response increased, indicating an increase in aqueous chemotherapeutic species present in solution; subsequently, when no current was introduced, the ORP value dropped, indicating that chemical intermediates were not being formed or were formed in decreased concentrations.

Example 7

Figure 8:
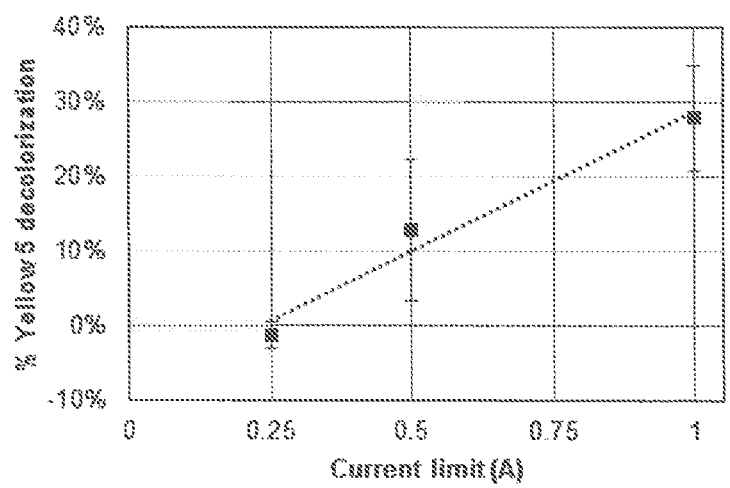
FIG. 8 is a graph of the oxidation of Yellow 5 dye as a function of applied current.
Figure 9:
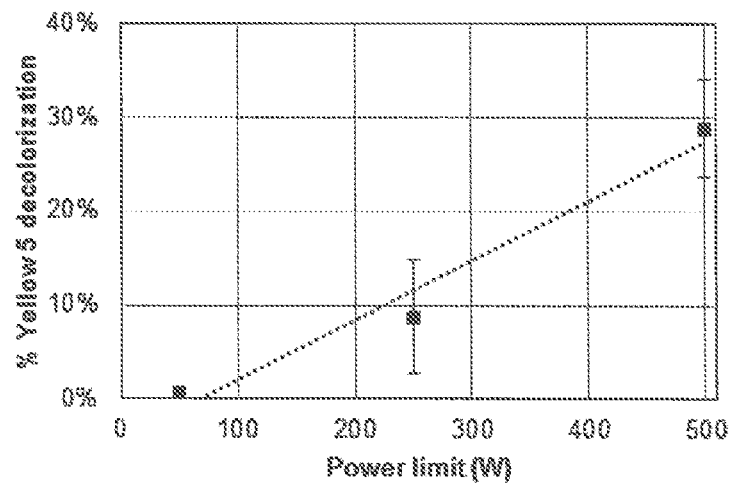
FIG. 9 is a graph of the oxidation of Yellow 5 dye as a function of applied power.

EXAMPLE 7 illustrates how the applied current/power impacts the oxidizing capacity of the species formed. The THDPR can be run under current or power control mode. In either case, an increase in the power or current applied to the system has been found to yield a linear increase in the oxidizing capacity of the system, as measured by chromophore loss (oxidation) of a model organic compound, Yellow 5. More specifically, FIG. 8 demonstrates how increasing the applied current from 0.25 A to 1 A yields a linear increase in oxidation of Yellow 5. Similarly, FIG. 9 shows how increasing the applied power from 50 to 500 W also yields a linear increase in the oxidation of Yellow 5.

Example 8

EXAMPLE 8 illustrates how the spin rate of the THDPR as related to system turbulence, impacts the oxidizing capacity of the system related to the species formed. Using the THDPR, which contains a central rotating array of negatively charged electrodes, the spin rate of the rotor was found to impact the oxidizing capacity of the system, as indicated by the oxidation of a surrogate organic compound, Methylene Blue, as measure spectroscopically. For influent solutions with a total dissolved solids level of 1000 mg/L, higher spin rates (1000 rpm) were found to result in ~20% greater organics oxidation compared to lower spin rates (700 rpm) for a given set of conditions. Thus, the spin rate of the rotor relating to the turbulence in the system may alter the distribution of the generated species in solution.

Example 9

EXAMPLE 9 illustrates how the TDS of the influent solution impacts the oxidizing capacity of the system related to the species formed. For the THDPR generating plasma under conditions in which the submersed pin electrodes are rotating at rates capable of inducing turbulent flow conditions within the reactor while applying an input current of 3 A and an aqueous solution residence time of approximately 2 min., a 2.5 mg/L TDS influent solution concentration resulted in the generation of 1 ppm hydrogen peroxide and a resultant effluent ORP value of 300 mV. When the TDS of the influent was increased to 1000 mg/L using NaCl, a 4 ppm concentration of hydrogen peroxide was generated with a final ORP of 560 mV, indicating that, under these operating conditions, an increase in TDS resulted in a subsequent increase in the chemical species formed in solution. Additionally, for these trials a surrogate organic compound, methylene blue, was added at 6 ppm into the influent solution and the resultant decrease in methylene blue concentration was measured via absorbance spectrophotometry as the species underwent reaction with the chemical species formed during operation of the plasma reactor. For the 2.5 mg/L TDS influent solution, a 15% reduction in methylene blue concentration was found, whereas the 1000 mg/L TDS solution yielded a 35% decrease in methylene blue. Since a variety of species that contribute to ORP with the potential to modify organic compounds also are responsible for the reaction of methylene blue, a larger percent decrease in methylene blue concentration indicates that greater chemical reactivity was observed in the higher TDS solution during plasma treatment.

Example 10

Figure 10:
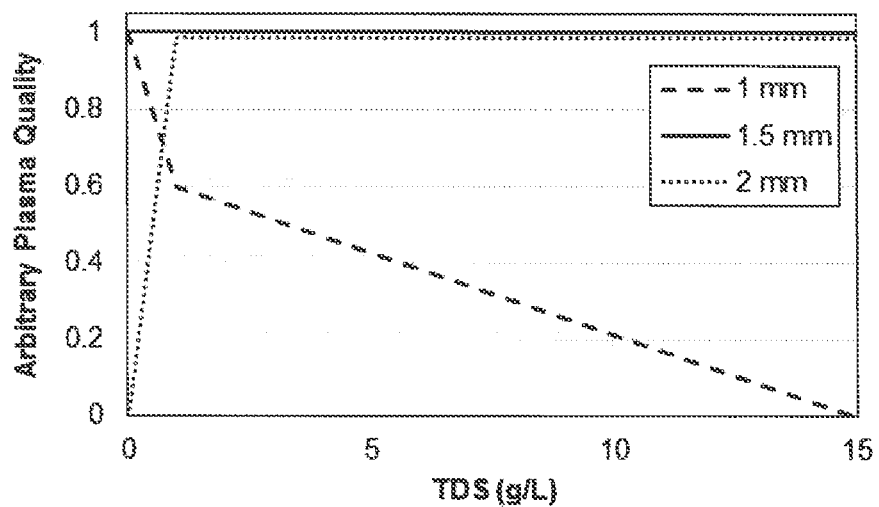
FIG. 10 is a graph of plasma quality as a function of total dissolved solids in solution for several electrode/cylinder wall spacings for the plasma generator, illustrating that the plasma quality, a qualitative score based on visualization of plasma discharge flashes through a transparent window into the THDPR, as well as data collection indicating steady power, voltage, and current parameters, is dependent on the total dissolved solids (TDS) of the influent solution, as well as on the electrode gap.

EXAMPLE 10 illustrates how the ability to generate plasma can be dependent upon both solution conductivity and electrode gap. For a given set of conditions, as shown in FIG. 10, an electrode separation distance of 1 mm restricted generation of plasma to influent solutions with less than about 5,000 mg/L TDS, while increasing the separation distance to 1.5 mm enabled plasma generation in influent solutions with 0-15,000 mg/L TDS. Further increasing the distance to 2 mm resulted in maintained plasma operation at greater than 15,000 mg/L, but would not enable plasma generation at <3 mg/L TDS. These data, when considered together, suggest that the ability to generate plasmas for a given electrode separation distance is dependent upon the influent TDS, where smaller separation distances enable plasma generation at zero-to-low TDS samples and an increase in separation enables plasma generation at higher TDS. Since variable ion concentrations due to the TDS level will impact the lifetime of intermediate species, the plasma processes that occur for different TDS solutions will impact the overall nature of the reactive species present in the final EPAAC solution. For example, reactive intermediates such as ozone are decomposed in the presence of chloride ion; thus, increasing chloride concentrations can decrease the lifetime of ozone in solution, which impacts the overall nature of the EPAAC solution and its ability to impact cellular processes.

Example 11

EXAMPLE 11 illustrates how the gas flow rate impacts the oxidizing capacity of the system related to the species formed. Using the THDPR configuration, the flow rate of house air into the reactor, where the air flow results in microbubbles forming at the tip of the electrode, dictates the resulting oxidizing capacity of the system, as measured by the chromophore loss of the organic compound, Yellow 5. When increasing the gas flow rate from 50 to 100 SCFH, an increase in the Yellow 5 chromophore loss was increased from 2 to 12.5%, respectively, under the same set of reaction conditions. This represents a linear region between 50 and 100 SCFH air flow rate where an increase in flow rate resulted in more oxidation. However, further increasing the air flow rate up to 200 SCFH did not yield any significant increase in oxidation compared to 100 SCFH. Thus, the gas flow rate may impact the oxidizing capacity of the system.

Example 12

EXAMPLE 12 illustrates the prolonged shelf-life of the APC solution. For commercial applications, the shelf-life of the APC solution product will dictate its mode of distribution into the market. Preliminary shelf-life results have indicated that APC solutions maintain the same physical properties as measured by oxidation-reduction potential, pH, TDS, and free chlorine, for solutions stored under refrigeration for 4 d, suggesting that 4 d is a lower limit for the shelf-life of these solutions. This is indirect evidence that the EPAAC solutions retain their chemotherapeutic activity for this period as well.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for treating pancreatic cancer, comprising:
providing a solution having a chosen quantity of sodium chloride dissolved in water;
providing an apparatus comprising: a chamber for containing said solution, said chamber having an electrically conducting cylindrical wall having an axis, an inlet for said solution at one end thereof and an outlet for said solution at the opposing end thereof; an elongated hollow, electrically conducting shaft rotatably disposed collinearly with the axis of the cylindrical portion of said chamber and having an open end and a closed end, the closed end thereof facing the end of said chamber having the inlet for the solution; at least one electrically conducting pin electrode having a bore therethrough, a first end and a second end, and having a frit effective for generating bubbles in said solution at the surface of said at least one pin electrode from which a plasma discharge is generated, disposed in the bore in the vicinity of the first end thereof, the second end being mounted through the surface of said shaft such that the bore of said at least one pin electrode is in gaseous communication with the interior of said hollow shaft; an electrically insulating cylinder having an axis collinear with the axis of said chamber disposed within said chamber, said electrically insulating cylinder having a surface through which a portion of said at least one pin electrode extends, said electrically insulating cylinder rotating with said shaft; a motor for rotating said shaft; a solution inlet for introducing said solution into the inlet of said chamber such that said solution flows axially in the cylindrical portion of said chamber; a gas source for introducing a chosen gas into the open end of said shaft at a pressure such that gas bubbles exit through said frit of said at least one pin electrode and rise in a counter-current manner to the flow of said solution; and an electrical power supply for applying a voltage to said shaft effective for initiating and maintaining said plasma discharge between the first end of said at least one pin electrode and the interior of the conducting cylindrical portion of said chamber;
introducing said solution into said chamber through said solution inlet;
introducing said chosen gas from said gas source into the open end of said shaft;
rotating said shaft at a chosen rotational rate using said motor;
applying a selected voltage from said power supply to said shaft, whereby a plasma discharge is generated;
exposing the solution to the plasma for a selected period of time, forming thereby a plasma activated solution having a pH; and
exposing cells afflicted with pancreatic cancer to said plasma activated solution.

2. The method of claim 1, wherein said step of exposing cells afflicted with pancreatic cancer further comprises the step of injecting said plasma activated solution into a pancreas.

3. The method of claim 1, wherein said step of exposing cells afflicted with pancreatic cancer further comprises the step of injecting said plasma activated solution into tissue surrounding a pancreas.

4. The method of claim 1, wherein said step of exposing cells afflicted with pancreatic cancer further comprises the step of intravenously injecting said plasma activated solution into a patient.

5. The method of claim 1, wherein said step of exposing cells afflicted with pancreatic cancer to said plasma activated solution further comprises the steps of adding a base to said plasma activated solution to adjust the pH to 7.4±0.1, forming thereby a physiological solution, and exposing cells afflicted with pancreatic cancer to said physiological solution.

6. The method of claim 5, wherein said step of exposing cells afflicted with pancreatic cancer to said physiological solution further comprises the step of injecting said physiological solution into a pancreas.

7. The method of claim 5, wherein said step of exposing cells afflicted with pancreatic cancer to said physiological solution further comprises the step of injecting said physiological solution into tissue surrounding a pancreas.

8. The method of claim 5, wherein said step of exposing cells afflicted with pancreatic cancer to said physiological solution further comprises the step of intravenously injecting said physiological solution into a patient.

9. The method of claim 1 wherein said step of exposing cells afflicted with pancreatic cancer to said plasma activated solution further comprises the steps of adding a base to said plasma activated solution to adjust the pH to 7.4±0.1, forming thereby a physiological solution, adding sodium chloride to said physiological solution to adjust the chosen quantity of sodium chloride to 9±0.1 g per liter of solution forming thereby an isotonic solution; and exposing cells afflicted with pancreatic cancer to said isotonic solution.

10. The method of claim 9, wherein said step of exposing cells afflicted with pancreatic cancer to said isotonic solution further comprises the step of injecting said isotonic solution into a pancreas.

11. The method of claim 9, wherein said step of exposing cells afflicted with pancreatic cancer to said isotonic solution further comprises the step of injecting said isotonic solution into tissue surrounding a pancreas.

12. The method of claim 9, wherein said step of exposing cells afflicted with pancreatic cancer to said isotonic solution further comprises the step of intravenously injecting said isotonic solution into a patient.

13. The method of claim 1, wherein treating pancreatic cancer comprises reducing proliferation of cells afflicted with pancreatic cancer.

14. The method of claim 13, wherein proliferation of normal cells is unaffected by said treatment of pancreatic cancer.

15. The method of claim 1, wherein said solution is recirculated through the plasma discharge.

16. The method of claim 1, wherein said chosen gas comprises air.

17. The method of claim 1, wherein the selected voltage is between about 250 V and about 750 V.

18. The method of claim 1, wherein the chosen quantity of said sodium chloride dissolved in water is 1 g/L.

19. The method of claim 1, wherein the first end of said at least one electrically conducting pin electrode is between about 0.5 mm and about 3 mm from the electrically conducting cylindrical wall of said chamber.

20. The method of claim 9, further including the step of centrifuging said isotonic solution.

21. The method of claim 9, further comprising the step of filtering said isotonic solution.

22. The method of claim 1, wherein the chosen rotational rate of said shaft is between about 60 rpm and about 5000 rpm.

* * * * *